United States Patent [19]

Redpath

[11] 4,134,359

[45] Jan. 16, 1979

[54] PACKAGE OF BIOLOGICALLY ACTIVE MATERIAL STORED AT A CRYOGENIC TEMPERATURE AT WHICH IT IS INACTIVE AND METHOD OF MAKING THE SAME

[75] Inventor: Donald J. Redpath, Norton, Mass.

[73] Assignee: United Aniline Co., Norwood, Mass.

[21] Appl. No.: 810,177

[22] Filed: Jun. 27, 1977

[51] Int. Cl.$^2$ ............................................. G01K 11/06
[52] U.S. Cl. ....................................... 116/219; 73/358; 128/DIG. 27
[58] Field of Search ............ 116/114.5, 114 V, 114 R; 73/358, 356, 354; 128/DIG. 27; 62/129, 130

[56] References Cited

U.S. PATENT DOCUMENTS 3,695,903   10/1972   Telkes ................................ 116/114.5

Primary Examiner—S. Clement Swisher
Assistant Examiner—Denis E. Corr

[57] ABSTRACT

The storage of material that is biologically active such as semen for use in artificial insemination, requires that it be held at a cryogenic temperature at which it is inactive. A package of such a material has a transparent container sealed at one end within which there is a frozen indicator of a color different than that of the material and which has a melting point close to but above a selected cryogenic temperature at which the material is inactive. A barrier is between the material and the indicator and of a type permeable by the indicator if melted and in storage, the indicator containing end of the container is uppermost. The volume of the indicator is such that if the indicator melts, it will flow through the barrier and irreversibly discolor the material as proof that proper storage conditions have not been maintained.

3 Claims, 9 Drawing Figures

PACKAGE OF BIOLOGICALLY ACTIVE MATERIAL STORED AT A CRYOGENIC TEMPERATURE AT WHICH IT IS INACTIVE AND METHOD OF MAKING THE SAME

BACKGROUND REFERENCES

U.S. Pat. Nos. 3,877,430, 3,090,236, 2,983,247, 2,856,585, 2,560,537, 2,046,863.

BACKGROUND OF THE INVENTION

The desirability of having means by which it will be apparent that a material has been exposed to an unsuitable temperture has, of course, been recognized.

As a consequence, such means of various types have been proposed to make apparent, for examples, that food has started to ferment, that sterilizing temperatures have not been attained, that the temperature of whole blood has not been maintained within appropriate limits, and that frozen foods have been subjected to thawing temperatures.

As far as I am aware, however, the means indicating that a material has been exposed to an improper temperature have always been affixed to the materials to give evidence of that fact but did not so affect the material that the material itself would provide that evidence.

Materials that are biologically active and are to be frozen for storage must be held at a cryogenic temperature at which they are biologically inactive. While the invention is adapted for use with a wide range of such materials, it is herein discussed primarily with reference to semen for use in artificial insemination, frozen and stored in tubular, plastic containers called straws and held in liquid nitrogen. While if melted and refrozen semen would not be fit to use, it has been established that at $-100°$ C. semen is biologically inactive but if exposed to temperatures much higher, it will start to deteriorate and become sub-standard. At the present time, there are no means to prevent sub-standard semen from being used.

THE PRESENT INVENTION

The general objective of the invention is to provide packaged biologically active material that, if it is to be frozen for later use, must be stored at a cryogenic temperature at which it is biologically inactive and will be irreversibly discolored if the packaged material has been so exposed to a temperature above the selected cryogenic temperature that the quality of the material may have been adversely affected.

In terms of the package, the package includes a substantially transparent container having a closed end that is to be the upper end during storage and in which end there is a predetermined volume of an indicator of a color different than that of the biologically active material and has a melting point close to but above the selected cryogenic storage temperature at which the material is biologically inactive. The container has a wanted volume of the material above the indicator and a barrier between the indicator and the material with the barrier permeable by the indicator if thawed. The volume of the indicator and its viscosity is such that if it melts, the indicator will flow through the barrier and discolor the material. The container is of a type such that the end thereof containing the indicator and the barrier can be readily detached if the color of the material, when it is to be used, is normal. While in one embodiment of the invention, there is a slight space between the indicator and the barrier, it is preferred that the barrier be in contact with the frozen indicator in order that, should the package be stored with the indicator below the material, the barrier would absorb and be irreversibly discolored by the indicator if it melted and irreversibly stain the proximate extremity of the material.

The indicators in accordance with the invention are any liquids or mixture thereof that have a melting point close to but above the cryogenic temperature at which the particular material being packaged is biologically inactive provided, of course, that the liquid will not react with the container or the barrier and has a viscosity such that it will readily flow through the barrier. If the liquid does not have a color different than that of the material, it must be a solvent for dyes by which it can be suitably colored. The term "cryogenic temperature", as used herein means a temperature at or below $-79°$ C.

In terms of method, the invention requires the steps of introducing into the closed end of the container the volume of the indicator that is adequate to ensure the discoloring of the material, the indicator of a color different than that of the material and having a melting point close to the cryogenic temperature at which the material is biologically inactive, and then freezing the indicator. A barrier, permeable by the indicator if it melts, is then seated against the frozen indicator and the wanted volume of the material then added and the open end of the container is closed. The material is now frozen and stored at a temperature at which it becomes and remains biologically inactive.

Alternatively, the indicator and material, with the barrier between them but with the barrier close to but spaced from the indicator, may be frozen at the same time if it is deemed unnecessary to ensure against the possibility of the package being stored, indicator end lowermost.

BRIEF DESCRIPTION OF THE DRAWINGS

In the accompanying drawings, a preferred embodiment of the invention is illustrated as a frozen semen package and the steps involved in its production and -

FIG. 9 is a fragmentary view showing the heat sealed end of a straw taken at right angles to the position of the straw in the other views.

THE PREFERRED EMBODIMENT OF THE INVENTION

Figure 1:
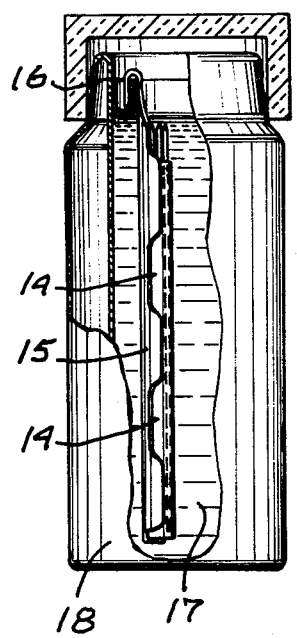
FIG. 1 is a schematic view illustrating the storage of frozen semen packages.
Figures 2, 3, 4, 5, 6, 7:
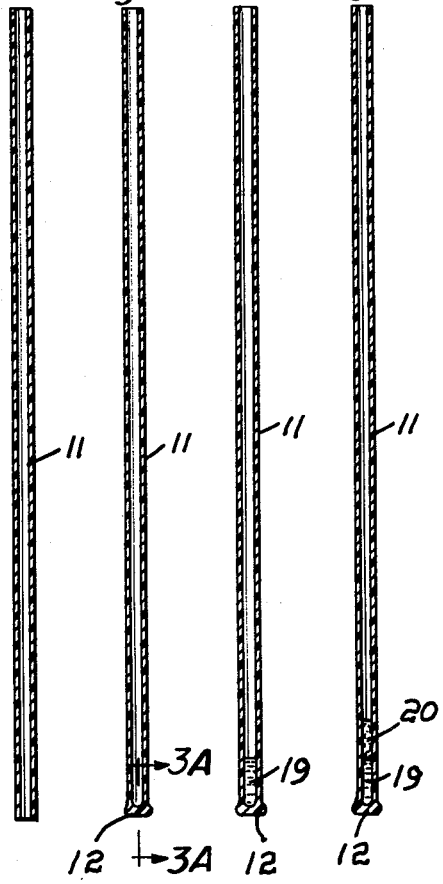
FIG. 2 is a longitudinal section, on a substantial increase in scale, of a so-called "straw" conventionally used in packaging frozen semen.
FIG. 3 is a view of the straw with one end heat sealed.
FIG. 4 is another like view with the colored indicator added.
FIG. 5 is a view illustrating the addition of the permeable barrier.
FIG. 6 is yet another like view showing the straw with the wanted volume of semen added.
FIG. 7 is a like view with the final and conventional step of placing a plug in the other end of the straw.
Figure 8:
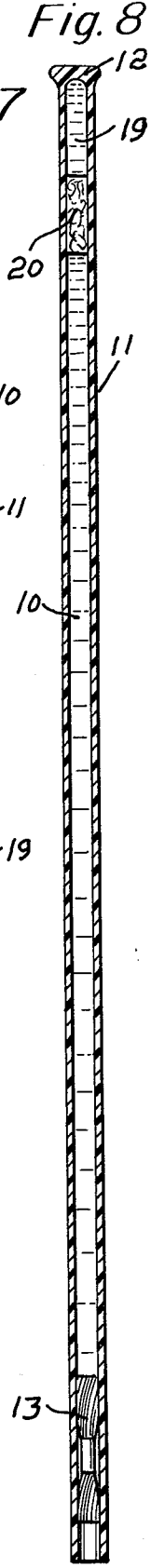
FIG. 8 is a longitudinal section, on an increase in scale of the package as it is positioned for storage.
Figure 3A:
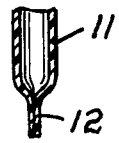

The usual practice in the storage of semen for use in the artificial insemination of animals is to place a predetermined volume of semen, generally indicated at 10, in a tubular substantially transparent container 11, commonly called a "straw" utilizing conventional filling apparatus. Each straw 11 is a length of a clear plastic tubing about five inches in length with an outside diameter in the neighborhood of one-eighth of an inch and closed at one end by a heat seal 12. After the semen 10 has been entered in a straw 11, its other end is closed by a plug 13.

Groups of such sealed straws are placed in holders 14 which are held vertically spaced by a rack 15, sometimes called a "cane", having a hook 16 at its upper end by which the rack is held with the straw suspended in a body 17 of liquid nitrogen in an insulated chamber 18 schematically illustrated by FIG. 1. Liquid nitrogen provides a cryostatic temperature enabling such semen-filled straws to be stored for at least several months without loss of potency when later used after having been appropriately thawed.

If, however, the semen had become partially thawed and then refrozen, it would have so deteriorated as to be unfit for use. In addition, the closer the temperature of the semen to its melting point, the shorter the storage period before the semen would become sub-standard. It is generally agreed, however, that if the temperature of the semen does not rise much above $-100°$ C., it will remain biologically inactive and therefore fit for later use when appropriately thawed.

In accordance with the present invention, the consequences to the user of failure to maintain the semen under proper storage is prevented, without interference with usual techniques in processing semen for later use, by providing an indicator of a color different than that of the semen and a melting point close to that regarded as the highest temperature that the semen is to be permitted to attain without being regarded as unfit for use. With a frozen volume 19 of such an indicator in the heat sealed end of a straw 11 and separated from the semen 10 by a barrier 20, cotton in practice, and with the straws stored, sealed end uppermost, the user is assured that the semen is fit to be used if of normal color. The volume of the indicator is such that should the temperature to which the semen is exposed be such as to melt the indicator 19, the indicator will flow through the barrier 20 and stain the semen 10.

In practice, the wanted volume of the indicator is introduced into a straw 11 using a conventional filling apparatus and frozen by dipping the straw for a few seconds in liquid nitrogen, inserting a cotton barrier 20 and seating it against the frozen indicator, then filling the straw with a predetermined volume of semen 10 and sealing its open end as with a cotton plug 13. The straw is then placed in a holder 14 with the heat sealed end 12 uppermost and the rack or cane suspended in the liquid nitrogen in the chamber 18.

While filling the straws 11 in this manner requires two steps, it has the advantage that should a straw be stored indicator-containing end lowermost and the straw then exposed to improper storage conditions, the melted indicator 19 would then be absorbed by the barrier 20 irreversibly discoloring it and irreversibly staining the lower portion of the semen.

If that particular feature is not wanted, the filling of the straw can be effected in a single operation with the barrier 20 spaced above but close to the unfrozen indicator with the indicator and the semen being frozen at the same time.

While the melting point and volume requirements of the indicator, and its color have been discussed, other requirements should be noted. The viscosity of the indicator must be such that it will be readily absorbed by and flow through the barrier 20 and it must of course be inert relative thereto and to the material from which the straws 11 are formed.

In the case of semen, the indicator must have a melting point close to but above the temperature at which semen becomes again biologically active and for that purpose appropriately dyed methanol is preferred as its melting point is $-97.8°$ C. Butanal $-99°$ C. may also be used.

For use with other biologically active materials, by way of illustration but not of limitation, other alcohols having higher or lower melting points below $-79°$ C. may be used as may esters, aldehydes, and ketones having melting points appropriate for the materials to be stored in a frozen state, such melting points being readily determined.

When a straw 11 is removed from storage, whether or not the semen has become discolored is immediately apparent. If not discolored, the straw is cut to remove the indicator 19 and the barrier 20 and is then used in a conventional manner after the semen has been thawed as by immersing it, plugged end lowermost, in warm water.

I claim:

1. The method of storing for later use semen that is biologically active but becomes inactive at a predetermined cryogenic temperature, said method consisting of the steps of introducing into the closed end of a substantially transparent tube having a closed end a predetermined volume of a liquid indicator that when frozen has a melting point at said predetermined cryogenic temperature and of a color different from that of the semen, placing in said tube a barrier that is permeable by the indicator when thawed, introducing a predetermined volume of semen into the tube, closing the other end of the tube, freezing the contents of the tube with said other end downward at a temperature in the neighborhood of $-100°$ C., and storing the tube with the indicator-containing end of the tube uppermost with a storage temperature such that the indicator and the semen are maintained in their frozen state, the volume of the indicator such that when thawed, the barrier is permeated and the semen immediately discolored as proof that the semen has been exposed to a temperature at which it may have become sub-standard, the tube being readily severable to permit the end of the tube containing the indicator and barrier to be removed if the color of the semen is normal.

2. The method of claim 1 in which the indicator is frozen before the barrier is inserted and seated against the frozen indicator.

3. A package of biologically active semen that becomes inactive at a predetermined cryogenic temperature in the neighborhood of $-100°$ C., said package including a substantially transparent tube having a closed end that is to be the upper end during storage, a frozen predetermined volume of an indicator in said closed end of a color different than that of semen and having a melting point close to but above said predetermined temperature, a frozen, wanted volume of the semen in said tube, a barrier between the indicator and the semen but spaced from the indicator, said barrier permeable by the indicator when and if thawed, and a closure at the other end of the tube, the volume of the indicator such that, if melted it will flow through the barrier and discolor the semen, the tube of a type enabling the end containing the indicator and the barrier to be readily detached if the color of the semen, when it is to be used, is normal.

* * * * *